United States Patent
Matsuno et al.

(10) Patent No.: US 8,962,705 B2
(45) Date of Patent: Feb. 24, 2015

(54) MATERIAL FOR REMOVING CAUXIN IN CAT URINE

(75) Inventors: Shinya Matsuno, Chiba (JP); Kyoichi Saito, Chiba (JP); Tetsuro Yamashita, Iwate (JP); Ayako Ito, Fukushima (JP); Yasuyuki Suzuta, Fukushima (JP)

(73) Assignees: National University Corporation Chiba University, Chiba (JP); Incorporated National University Iwate University, Iwate (JP); Nippon Zenyaku Kogyo Co., Ltd., Fukushima (JP)

( * ) Notice: Subject to any disclaimer, the term of this patent is extended or adjusted under 35 U.S.C. 154(b) by 236 days.

(21) Appl. No.: 13/579,897

(22) PCT Filed: Feb. 17, 2011

(86) PCT No.: PCT/JP2011/054062
§ 371 (c)(1),
(2), (4) Date: Oct. 24, 2012

(87) PCT Pub. No.: WO2011/102540
PCT Pub. Date: Aug. 25, 2011

(65) Prior Publication Data
US 2013/0041054 A1  Feb. 14, 2013

(30) Foreign Application Priority Data

Feb. 17, 2010 (JP) ................................ 2010-032990

(51) Int. Cl.
| | | |
|---|---|---|
| *C08F 255/02* | (2006.01) |
| *C08F 257/02* | (2006.01) |
| *C08F 259/00* | (2006.01) |
| *C08F 263/04* | (2006.01) |
| *C08F 283/04* | (2006.01) |
| *C08J 9/36* | (2006.01) |
| *G01N 33/68* | (2006.01) |
| *C12Q 1/44* | (2006.01) |

(52) U.S. Cl.
CPC .............. *G01N 33/6893* (2013.01); *C12Q 1/44* (2013.01); *G01N 2333/918* (2013.01); *G01N 2800/347* (2013.01)
USPC ............................... 521/53; 436/86; 525/286

(58) Field of Classification Search
None
See application file for complete search history.

(56) References Cited

U.S. PATENT DOCUMENTS

| 2004/0214171 A1 | 10/2004 | Yamashita et al. |
| 2010/0190262 A1 | 7/2010 | Yamashita et al. |

FOREIGN PATENT DOCUMENTS

| JP | 2003-250575 A | | 9/2003 |
| JP | WO-2009/013839 A1 | | 1/2009 |
| JP | 2009-101289 A | | 5/2009 |
| JP | 2009-101289 A | * | 5/2009 |
| WO | WO 2006/082059 A1 | | 8/2006 |

OTHER PUBLICATIONS

Ashour M-B A. et al., "Apparent Induction of Microsomal Carboxylesterase Activities in Tissues of Clofibrate-Fed Mice and Rats", Toxicology and Applied Pharmacology, Jul. 1987, pp. 361-369, vol. 89, No. 3.
Ashour M-B A. et al., "Substituted Trifluoroketones as Potent, Selective Inhibitors of Mammalian Carboxylesterases", Biochemical Pharmacology, Jun. 15, 1987, pp. 1869-1879, vol. 36, No. 12.
Matsuno Shin'ya et al., "Nyo Kensa no yoru Neko no Jinzobyo Shindan o Kano ni suru Nyochu Tanpakushitsu cauxin Sentaku Jyokyoyo Takoseimaku no Kaihatsu", Abstracts of Annual Meeting of Membrane Society of Japan, May 1, 2010. p. 53, vol. 32.
Wheelock C. E. et al., "Synthesis of New Carboxylesterase Inhibitors and Evaluation of Potency and Water Solubility", Chemical Research in Toxicology, Dec. 2001, pp. 1563-1572, vol. 14, No. 12.
International Search Report of PCT/JP2011/054062 dated Mar. 29, 2011.
Supplementary European Search Report dated Nov. 18, 2013, in EP 11744823.3.
Hanzlik et al., "Characterization of Affinity-purified Juvenile Hormone Esterase from *Trichoplusia ni*," J. Biol. Chem., Oct. 5, 1987, 262(28):13584-13591.
Szekacs et al., "An Affinity-Amplified Immunoassay for Juvenile Hormone Esterase," Analytical Biochemistry, Dec. 1, 1992, 207(2):291-297.
Thomas et al., "Affinity Chromatography of Neuropathy Target Esterase," Chem. Biol. Interactions, Jun. 1, 1993, 87(1-3):347-360.

* cited by examiner

*Primary Examiner* — Robert Sellers
(74) *Attorney, Agent, or Firm* — Foley & Lardner LLP (57) ABSTRACT

A method for removing cauxin in cat urine and a material for removing cauxin are provided. The material for removing cauxin in cat urine comprises a polymer substrate on which surface a trifluoroketone derivative is immobilized via dithiol.

5 Claims, 8 Drawing Sheets

MATERIAL FOR REMOVING CAUXIN IN CAT URINE

CROSS-REFERENCE TO RELATED APPLICATIONS

This application is a national phase of International application PCT/JP2011/054062, filed Feb. 17, 2011, which was published on Aug. 25, 2011, as WO 2011/102540, which claims the benefit of JP Appln No. 2010-032990, filed Feb 17, 2010. In their entirety, the respective contents of these documents are incorporated herein by reference.

TECHNICAL FIELD

The present invention relates to diagnosis of renal dysfunction in cats through detection of proteinuria in cats, a method for removing cauxin, which is a physiological protein in cat urine, and a material for removing cauxin.

BACKGROUND ART

Cats raised as pets are particularly susceptible to kidney disease once they become old. Cat kidney disease ranks as the highest cause of death among cats, and thus early diagnosis thereof is an important issue for small animal veterinarians at clinical sites. In the case of humans, the levels of proteins excreted in urine are measured for initial diagnosis of kidney disease. Proteinuria is used as a diagnostic marker for early warning of kidney abnormalities. However, in the case of cats, cauxin (carboxylesterase-like urinary excreted protein), which is a kidney-derived protein and a kind of carboxylesterase that has a molecular weight of 70 kDa, is present at a high concentration in urine, even in the cases of healthy cats. Hence, physiological proteinuria (Cauxin urine) and pathological proteinuria are indistinguishable with the use of a commercially available urine test paper strip. The concentration of cauxin in cat urine is as high as 0.50 g/L, and a cat excretes 100 mg of cauxin a day.

Therefore, diagnosis of cat kidney disease requires the removal of cauxin from urine, and thus a pretreatment material therefor is required.

A method using lectin that specifically binds to the sugar chain of cauxin has been reported as a method for removing cauxin from cat urine (see Patent Document 1).

PRIOR ART DOCUMENTS

Patent Documents

Patent Document 1 International Patent Publication WO2009/013839 pamphlet

SUMMARY OF INVENTION

An object of the present invention is to provide a method for removing cauxin in cat urine using a trifluoroketone derivative as a ligand and a material for removing cauxin.

Methods for removing cauxin in cat urine using lectin are problematic in that lectin is expensive and realization of a high volume of a material for removing cauxin is difficult.

Accordingly, the present inventors have intensively studied the development of a material for removing cauxin in cat urine as an alternative to lectin. The present inventors have prepared and examined a material for removing cauxin by binding a trifluoroketone (TFK) derivative that binds to a substrate pocket of carboxylesterase so as to function as an inhibitor to a substrate through radiation-induced graft polymerization in consideration of the ability of cauxin (a kind of carboxylesterase) to bind to the active center of a carboxylesterase inhibitor. As a result, the present inventors have discovered that TFK (a low-molecular weight compound) can ensure sufficient space for cauxin adsorption, making it advantageous in realization of a high volume of a material for removing cauxin, and thus they have completed the present invention. The use of TFK has another advantage in that the purification material can be prepared at a cost lower than is possible with the use of expensive lectin.

Specifically, the present invention is as follows.

[1] A material for removing cauxin in cat urine, wherein a trifluoroketone derivative having carboxyesterase inhibiting activity is immobilized via dithiol to the surface of a polymer substrate.

[2] The material for removing cauxin in cat urine of [1], wherein the side chain of a trifluoroketone derivative having carboxyesterase inhibiting activity represented by either formula (VII) or (VIII) below is immobilized to the surface of the polymer substrate, (VII)

[wherein X is a $C_{1-12}$ hydrocarbon chain and preferably a $C_{2-5}$ hydrocarbon chain, Y is a saturated or unsaturated $C_{1-12}$ and preferably $C_{1-5}$ hydrocarbon chain that may be substituted with fluorine, A is —S—, —SO—, —OSO—, —Se—, —SeO—, or —OSeO—, and B is —$CF_3$, —$CF_2H$, —$CH_2F$, or —$CH_3$.]

(VIII)

[wherein X is a $C_{1-12}$ hydrocarbon chain and preferably a $C_{2-5}$ hydrocarbon chain, Y is a saturated or unsaturated $C_{2-12}$ and preferably $C_{2-5}$ hydrocarbon chain, A is —S—, —SO—, —OSO—, —Se—, —SeO—, or —OSeO—, and B is —$CF_3$, —$CF_2H$, —$CH_2F$, or —$CH_3$.]

[3] The material for removing cauxin in cat urine of [2], wherein in the side chain represented by formula (VII) or (VIII), X is —$(CH_2)_n$— [where n ranges from 1 to 12], A is —S—, —SO— or —OSO—, Y is —$(CH_2)_m$— [where m ranges from 1 to 12], and B is —$CF_3$.

[4] The material for removing cauxin in cat urine of [2], wherein the side chain represented by formula (VII) or (VIII) is any one of side chains represented by the following formulae (IX) to (XII),

(IX)

(X)

(XI)

(XII)

[in the side chains represented by formulae (IX) to (XII), X is —$(CH_2)_n$— [where n ranges from 1 to 12], and m ranges from 1 to 12].

[5] The material for removing cauxin in cat urine of any one of [1] to [4], wherein the polymer substrate is a porous polyethylene hollow-fiber membrane.

[6] The material for removing cauxin in cat urine of any one of [1] to [4], wherein the polymer substrate is a porous polyethylene sheet.

[7] A method for producing a material for removing cauxin in cat urine, comprising the steps of:
(i) binding glycidyl methacrylate to a polymer substrate through graft polymerization so as to introduce epoxy groups onto the surface of the polymer substrate;)
(ii) reacting dithiol with trifluoroketone bromide in the presence of isopropanol so as to prepare trifluoroketone having thiol groups; and
(iii) reacting the epoxy groups introduced onto the polymer substrate in step (i) with the thiol groups of trifluoroketone prepared in step (ii), so as to convert the epoxy groups to trifluoroketone groups.

[8] The method of [7], wherein the polymer substrate is a porous polyethylene hollow-fiber membrane.

[9] The method of [7], wherein the polymer substrate is a porous polyethylene sheet.

[10] The method of any one of [7] to [9], wherein dithiol is 1,2-ethanedithiol and trifluoroketone bromide is 3-bromo-trifluoropropan-2-one.

[11] A kit for detecting a urinary protein resulting from cat kidney dysfunction, comprising the material for removing cauxin in cat urine of any one of [1] to [6].

A cat urine test using a protein test paper strip, which is used for general examination of urine, distinguishes with difficulty between cauxin existing in a large amount in healthy urine and urinary proteins resulting from kidney disorder (renal dysfunction). Through measurement with the use of the material for removing cat cauxin of the present invention, it is possible to selectively detect the latter urinary proteins alone. Also, since a trifluoroketone derivative, which is a low molecular weight compound, is used for the material for removing cauxin in cat urine of the present invention, the volume of the material can be increased. Cauxin can be removed from a small amount of a specimen, cauxin can be efficiently removed from a small amount of cat urine, and the subsequent examination of urine using a protein test paper strip can also be efficiently conducted. Furthermore, the material for removing cauxin of the present invention can be produced inexpensively.

This description includes part or all of the contents as disclosed in the description and/or drawings of Japanese Patent Application No. 2010-032990, which is a priority document of the present application.

BRIEF DESCRIPTION OF DRAWINGS

FIG. 5 shows the protein distribution (FIG. 5(a)) in effluents from the C2TFK membrane and the intensity of CE activity (FIG. 5(b)).

EMBODIMENTS FOR CARRYING OUT THE INVENTION

Hereafter, the present invention will be described in detail.

A material for selective adsorption and removal of cauxin from cat urine comprises a substrate, a graft polymer chain bound to the substrate, and a trifluoroketone derivative immobilized to the graft polymer chain. The trifluoroketone derivative acts as a carboxylesterase (CE) inhibitor, so as to enter the active center of cauxin that is carboxylesterase and to inhibit the initiation of the reaction, so that cauxin is selectively adsorbed.

An example of the substrate is a polymer substrate. Such a polymer substrate that can be used herein may be particulate, membranous, sheet-shaped, or fibrous. Examples of a polymer substrate include polyolefin such as polyethylene and polypropylene, halogenated polyolefin such as polyvinylidene fluoride, a copolymer of polyolefin and fluororesin, ethylene-vinyl acetate copolymer, polystyrene, and nylon. In particular, polyethylene is preferred. In the case of particulate polymer substrate, the mean particle diameter ranges from 10 µm to 80 µm, and preferably ranges from 20 µm to 60 µm. An example of a membranous or sheet-shaped polymer substrate is a porous body having pores in communication with each other. The mean pore size of such a porous body preferably ranges from 0.5 µm to 5 µm and the thickness thereof ranges from preferably 1 mm to 10 mm. Also, the pore volume fraction preferably ranges from 70% to 85%. As a porous body having such pores, for example, a porous polyethylene hollow-fiber membrane or a porous polyethylene sheet is used. In the present invention, binding to the surface of a polymer substrate includes binding to the surfaces within pores of a porous polymer material.

A graft polymer chain is prepared by binding a polymer chain having functional groups to the above substrate by a graft polymerization method. The graft polymerization method involves causing the uniform generation of radicals on a substrate and performing graft polymerization of monomers using the radicals as initiating points, so as to grow (bind) the polymer chain. In graft polymerization, radicals are generated by irradiation such as ionized radiation of α rays, β rays, γ rays, an electron beam, or the like. Also, ultraviolet rays or a polymerization initiator can be used. Polymerizable monomers forming a graft polymer chain having functional groups are not particularly limited, as long as they can convert the functional groups to functional groups for adsorption. An example of a functional group is an epoxy group. Examples of a polymerizable monomer include glycidyl methacrylate (GMA) and glycidyl acrylate that are polymerizable monomers having epoxy groups. To immobilize a graft polymer having functional groups to a substrate with appropriate density, the amount of radicals (functioning as initiators for graft polymerization) generated should be adjusted to be within an appropriate range. The dose of exposure of a substrate to radiation or the like is adjusted for this purpose. The exposure dose ranges from, when a substrate is polyethylene, 10 kGy to 250 kGy, and preferably ranges from 10 kGy to 100 kGy. The degree of grafting [100 (the mass of GMA chain introduced)/(the mass of PE membrane)] upon graft polymerization preferably ranges from about 100% to 150%. With a degree of grafting of 100% or less, the polyethylene surface of the substrate is exposed, so that non-specific protein adsorption can take place. With a degree of grafting of 150% or more, the strength of the substrate is lowered and the cut surface becomes cracked upon cutting of the thus obtained membrane, resulting in lowered processability. Functional groups such as epoxy groups are introduced onto the surface of a polymer substrate through graft polymerization.

Such a method for binding a polymer chain to a substrate through the graft polymerization method is described in JP Patent Publication (Kokai) No. 2007-45906 and JP Patent Publication (Kokai) No. 2009-101289 and can be performed according thereto.

Subsequently, a trifluoroketone derivative is bound to the substrate to which the polymer chain having functional groups has been bound. When a polymer chain is glycidyl methacrylate, a trifluoroketone (TFK) derivative having thiol groups may be bound. Examples of such a trifluoroketone derivative having thiol to be used herein include trifluoroketone having thiol groups, gem-diol having hydrated carbonyl groups, or an analog such as a methyl analog wherein —$CF_3$ of trifluoroketone or gem-diol is substituted with —$CF_2H$, —$CH_2F$, or —$CH_3$. An example thereof is a ketone compound represented by the following general formula (I). A trifluoroketone derivative that can be used in the present invention has carboxyesterase inhibiting activity.

SH—X-A-Y—CO—B  (I)

[wherein X is a $C_{1-12}$ hydrocarbon chain and preferably a $C_{2-5}$ hydrocarbon chain, Y is a saturated or unsaturated $C_{1-12}$ and preferably $C_{1-5}$ hydrocarbon chain that may be substituted with fluorine, A is —S—, —SO—, —OSO—, —Se—, —SeO—, or —OSeO—, and B is —$CF_3$, —$CF_2H$, —$CH_2F$, or —$CH_3$.]

Also, X is preferably —$(CH_2)_n$— [where n is an integer between 1 and 12, preferably an integer between 2 and 5, and further preferably 2]. Also, A is preferably —S—, —SO—, or —OSO—, and is further preferably —S—. Also, Y is preferably —$(CH_2)_m$— [where m is an integer between 1 and 12, preferably an integer between 1 and 5, and further preferably 1]. Furthermore, B is preferably —$CF_3$.

Examples of a trifluoroketone derivative having thiol groups represented by general formula (I) include: a compound represented by

SH—X—S—$CH_2$—CO—$CF_3$  (II)

[wherein X is a $C_{1-12}$ hydrocarbon chain, preferably a $C_{2-5}$ hydrocarbon chain, and further preferably —$(CH_2)_n$— [where n is an integer between 1 and 12, preferably an integer between 2 and 5, and further preferably 2]]; and a compound represented by

SH—X—OSO—$CH_2$—CO—$CF_3$  (III)

[wherein X is a $C_{1-12}$ hydrocarbon chain, preferably a $C_{2-5}$ hydrocarbon chain, and further preferably —$(CH_2)_n$— [where n is an integer between 1 and 12, preferably an integer between 2 and 5, and further preferably 2]].

Furthermore, a trifluoroketone derivative having thiol groups contains a gem-diol compound represented by the following general formula (IV).

SH—X-A-Y—$C(OH)_2$—B  (IV)

[wherein X is a $C_{1-12}$ hydrocarbon chain and preferably a $C_{2-5}$ hydrocarbon chain, Y is a saturated or unsaturated $C_{2-12}$ and preferably $C_{2-5}$ hydrocarbon chain that may be substituted with fluorine, A is —S—, —SO—, —OSO—, —Se—, —SeO—, or —OSeO—, and B is —$CF_3$, —$CF_2H$, —$CH_2F$, or —$CH_3$.]

Also, X is preferably —$(CH_2)_n$— [where n is an integer between 1 and 12, preferably an integer between 2 and 5, and further preferably 2]. Also, A is preferably —S—, —SO—, or —OSO—, and further preferably —S—. Also, Y is preferably —$(CH_2)m$- [where m is an integer between 1 and 12, preferably an integer between 1 and 5, and further preferably 1]. Furthermore, B is preferably —$CF_3$.

An example of a trifluoroketone derivative having thiol groups represented by general foiinula (II) is a compound represented by

SH—X—S—$CH_2$—$C(OH)_2$—$CF_3$  (V)

[wherein X is a $C_{1-12}$ hydrocarbon chain, preferably a $C_{2-5}$ hydrocarbon chain, and further preferably —$(CH_2)_n$— [where n is an integer between 1 and 12, preferably an integer between 2 and 5, and further preferably 2]].

A trifluoroketone derivative having thiol groups can be synthesized by mixing a trifluoroketone bromide derivative with dithiol represented by the following general formula (V) in an organic solvent.

HS—X—SH  (VI)

[wherein X is a $C_{1-12}$ hydrocarbon chain, preferably a $C_{2-5}$ hydrocarbon chain, and further preferably —$(CH_2)_n$— [where n is an integer between 1 and 12, preferably an integer between 2 and 5, and further preferably 2]].

For example, as dithiol, 1,2-ethanedithiol (C2DT) wherein "n" is 2 in the above general formula (I) can be used. As trifluoroketone bromide, 3-bromo-trifluoropropane-2-one (TFA) represented by structural formula shown in FIG. 2 can be used. 1,2-ethanedithiol (C2DT) and 3-bromo-trifluoropropane-2-one (TFA) are mixed in an organic solvent for reaction, and thus 1,1,1-trifluoro-3-(2-sulfanylethylsulfanyl)propane-2-one (C2TFK) that is trifluoroketone having thiol groups can be synthesized.

Examples of an organic solvent to be used for synthesis of a trifluoroketone derivative having thiol groups include isopropanol, carbon tetrachloride, ethyl acetate, and dioxane. A high molar conversion rate can be obtained when particularly isopropanol or carbon tetrachloride is used and isopropanol is preferred in view of environmental safety.

Dithiol and a trifluoroketone derivative are mixed at a molar ratio ranging from 1:1 to 1:2 and preferably ranging from 1:1 to 1:1.2, followed by 10 to 72 hours and preferably 24 to 60 hours of reaction under a nitrogen atmosphere at room temperature. Hence, a trifluoroketone derivative having thiol groups can be obtained.

A substrate to which the above polymer chain has been bound is immersed in a solution containing the trifluoroketone derivative having the thiol group(s), so that epoxy groups in the substrate are converted to trifluoroketone derivative groups. The time for immersion at this time ranges from 2 to 72 hours and preferably ranges from 10 to 60 hours. The molar conversion rate (100 (the number of moles of the introduced TFK groups)/(the number of moles of epoxy groups before reaction)) for the trifluoroketone group is preferably 8% or more, further preferably 25% or more, and even further preferably 30% or more. After conversion of epoxy groups to trifluoroketone derivative groups, unconverted epoxy groups remain. When epoxy groups remain unhydrophilized, proteins may be adsorbed thereto non-specifically. Accordingly, remaining epoxy groups are preferably converted to diol groups. Epoxy groups are converted to diol groups by adding water to the epoxy groups of a substrate (e.g., by immersing a substrate to which a trifluoroketone derivative has been bound in sulfuric acid). In the present invention, a substrate prepared by binding 1,1,1-trifluoro-3-(2-sulfanylethylsulfanyl)propane-2-one (C2TFK) and converting the remaining epoxy groups to diol groups is referred to as a C2TFK-diol substrate.

A membrane or sheet can be prepared by the method having the density of the trifluoroketone derivative group ranging from 50 to 1000 μmol/mL, preferably ranging from 50 to 500 μmol/mL, and further preferably ranging from 50 to 360 μmol/mL per volume of the membrane or sheet.

The thus prepared material for removing cat cauxin comprises a polymer hollow-fiber membrane, a porous polymer sheet, or the like to which the side chain represented by either the following formula (VII) or (VIII) is bound.

(VII)

[wherein X is a $C_{1-12}$ hydrocarbon chain and preferably a $C_{2-5}$ hydrocarbon chain, Y is a saturated or unsaturated $C_{1-12}$ and preferably $C_{1-5}$ hydrocarbon chain that may be substituted with fluorine, A is —S—, —SO—, —OSO—, —Se—, —SeO—, or —OSeO—, B is —$CF_3$, —$CF_2H$, —$CH_2F$, or —$CH_3$.]

Also, X is preferably —$(CH_2)_n$— [where n is an integer between 1 and 12, preferably an integer between 2 and 5, and further preferably 2]. Also, A is preferably —S—, —SO—, or —OSO—, and is further preferably —S—. Also, Y is preferably —$(CH_2)_m$— [where m is an integer between 1 and 12, preferably an integer between 1 and 5, and further preferably 1]. Furthermore, B is preferably —$CF_3$.

(VIII)

[wherein X is a $C_{1-12}$ hydrocarbon chain and preferably a $C_{2-5}$ hydrocarbon chain, Y is a saturated or unsaturated $C_{2-12}$ and preferably $C_{2-5}$ hydrocarbon chain that may be substituted with fluorine, A is —S—, —SO—, —OSO—, —Se—, —SeO—, or —OSeO—, and B is —$CF_3$, —$CF_2H$, —$CH_2F$, or —$CH_3$.]

Also, X is preferably —$(CH_2)_n$— [where n is an integer between 1 and 12, preferably an integer between 2 and 5, and further preferably 2]. Also, A is preferably —S—, —SO—, or —OSO—, and is further preferably —S—. Also, Y is preferably —$(CH_2)m$- [where m is an integer between 1 and 12, preferably an integer between 1 and 5, and further preferably 1]. Furthermore, B is preferably —$CF_3$.

Examples of the above side chains include side chains represented by the following formulae (IX) to (XII), for example.

In side chains represented by formulae (IX) to (XII), X is a $C_{1-12}$ hydrocarbon chain, preferably a $C_{2-5}$ hydrocarbon chain, and further preferably —$(CH_2)_n$— [where n is an integer between 1 and 12, preferably an integer between 2 and 5, and further preferably 2, m is an integer between 1 and 12, preferably an integer between 1 and 5, and further preferably 1]. Also, a side chain (diol groups converted from remaining epoxy groups) represented by the following formula (XIII) is further bound thereto.

(XIII)

Cauxin can be removed from cat urine using the material for removing cat cauxin prepared by the above method. For removal of cauxin from cat urine, the material for removing cat cauxin is brought into contact with cat urine, and then cat cauxin is adsorbed to the material for removing cauxin. Contact of cat urine with the material for removing cauxin may be performed by: adding the material for removing cauxin and cat urine to a container and then performing a batch method; causing cat urine to pass through a membrane or sheet to which the trifluoroketone derivative has been bound; or filling a column or the like with the material for removing cauxin and then causing cat urine to pass through the column. When such a membrane or sheet is used, the membrane is incorporated to anywhere between a liquid inlet and a liquid outlet of a device, cat urine is applied to the device via the liquid inlet, and it is then caused to pass through the membrane or sheet when it is discharged from the liquid outlet. When a column is used, a mini-column is desirably used in order to enable detection of a urinary protein when even a small amount of cat urine is used. The capacity of such a mini-column ranges from 100 μL to 2000 μL, for example. For example, the tip of a commercially available micropipette chip (blue chip or yellow chip) made of a resin such as polypropylene is filled with absorbent cotton, filter paper, or the like and then with a carrier to which a substance specifically binding to cauxin has been bound, so that a mini-column for removing cauxin is prepared. Cat urine is added to the mini-column and then urine that has passed through the column is collected, so that cat urine from which cauxin has been removed can be obtained. Furthermore, a device integrated with a membrane or a column filled with the material for removing cat cauxin is designed so that it can be connected to a syringe, and then cat urine collected in the syringe is caused to pass through the device or the column. Thus, urine from which cauxin has been removed can be obtained.

In the present invention, such a column or the like filled with a material for removing cat cauxin may also be referred to as a device for removing cat cauxin, a column for removing cat cauxin, or a chip for removing cat cauxin.

At this time, the ratio of the amount of cat urine to the amount of a substance specifically binding to cauxin is not limited. Cat urine may be caused to come into contact with such a substance at a ratio that allows cauxin in cat urine to be completely removed. Cauxin is present in the urine of a healthy cat in an amount of about 0.9 mg/mL, but is present in the urine of a cat with renal dysfunction in an amount of about 0.1 mg/mL or less. Treatment is performed with the method of the present invention, so that 90% or more and preferably 95% or more of the amount of cauxin existing in the urine of a healthy cat is removed. 50 µL to 200 µL, and preferably 100 µL, of cat urine is used for a single measurement.

For detection of renal dysfunction of a cat, proteins in cat urine from which cauxin has been removed are measured. Examples of proteins that can be markers for renal dysfunction include albumin, lysozyme, and haptoglobin.

Urinary proteins can be measured using a test paper strip for measuring urinary proteins.

As a test paper strip for measuring urinary proteins, a commercially available known test paper strip may be used. An example of such a commercially available test paper strip is a pretest (Wako Pure Chemical Industries, Ltd.). This test paper strip impregnated with a pH indicator (e.g., bromphenol blue or tetrabromophenol blue) and pH buffer (e.g., citrate buffer) is used for detecting proteins based on the protein error of the pH indicator.

Also, detection can be performed by a Bradford method, a BCA protein quantification method, a sulfosalicylic acid method, or the like.

In the case of cats, they can be diagnosed as having or not having kidney disorder on the basis of the concentrations of proteins in urine from which cauxin has been removed. When the concentration of a protein in cat urine ranges from about 100 to several hundred µg/mL, and preferably ranges from about 100 to about 200 µg/mL or more, it likely has kidney disorder. Finally a veterinarian judges in a comprehensive manner if it has kidney disorder.

According to the method of the present invention, renal dysfunction-derived proteins in cat urine can be detected, and thus cat renal dysfunction can be diagnosed.

The term "cat(s)" in the present invention refers to an animal(s) belonging to the family Felidae. Examples of cats to be used herein include animals belonging to Felidae (the subfamily of the family Felidae), such as domestic cats, pumas, and wild cats, animals belonging to the Pantherinae (the subfamily of the family Felidae) such as leopard, lion, tiger, and jaguar, and animals belonging to the genus *Acinonyx* of the family Felidae, such as cheetah (*Acinonyx jubatus*).

Furthermore, the present invention encompasses a kit for detecting urinary proteins resulting from cat kidney dysfunction or a kit for diagnosis of cat kidney disease, which comprises the above material for removing cauxin or device containing the same. Such a kit may comprise a test paper strip for detecting urinary proteins.

The present invention further encompasses the use of the above trifluoroketone derivative as an inhibitor for inhibiting cauxin activity. For example, a trifluoroketone derivative that is a cauxin-specific inhibitor is added in advance to a cat urine (collection) receptacle, cauxin is then inactivated, and thus leukocyte activity can be determined.

The present invention further encompasses a trifluoroketone derivative-containing agent for preventing the generation of cat urine odor. The agent for preventing the generation of cat urine odor contains a trifluoroketone derivative as an active ingredient and inhibits cauxin; that is, carboxylesterase, a possible cause of cat urine odor.

Hereafter, the present invention is described in greater detail with reference to the examples, although the present invention is not limited to the examples.

EXAMPLE 1

Figure 1:
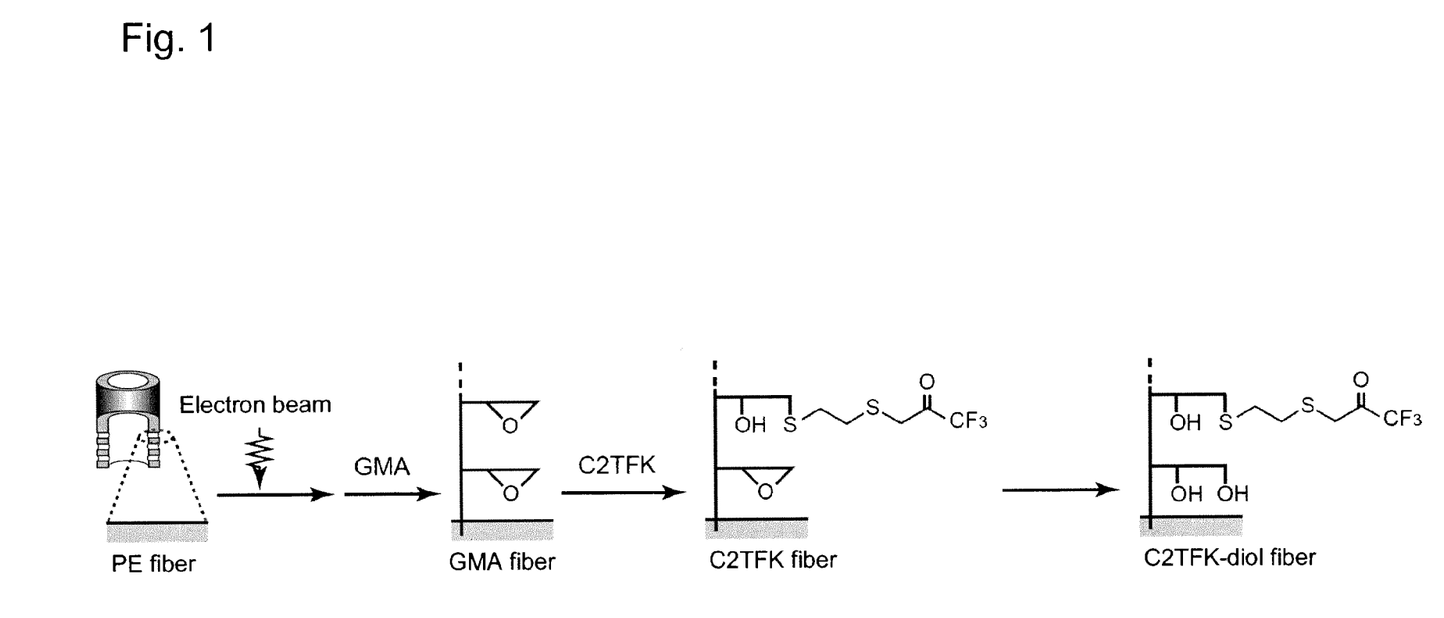
FIG. 1 shows a pathway for immobilization of trifluoroketone to a porous hollow-fiber membrane.

Evaluation of the Cauxin Removal Performance (for Removing Cauxin from Cat Urine) of a Material for Removing Cauxin Prepared Using a Porous Hollow-fiber Membrane as a Substrate Methods
1. Immobilization of a Carboxylesterase Inhibitor having Thiol Groups to a Porous Hollow-fiber Membrane FIG. 1 shows a pathway for immobilization of TFK to a porous hollow-fiber membrane. First, a porous polyethylene hollow-fiber membrane (mean pore size: 0.36 µm) was irradiated with an electron beam (200 kGy) for polymerization of glycidyl methacrylate (GMA), which is a monomer having epoxy groups. The thus obtained membrane is referred to as a GMA membrane. The degree of grafting was defined by the following formula (1), and it was then calculated based on an increase in the weight of the membrane following graft polymerization.

Figure 2:
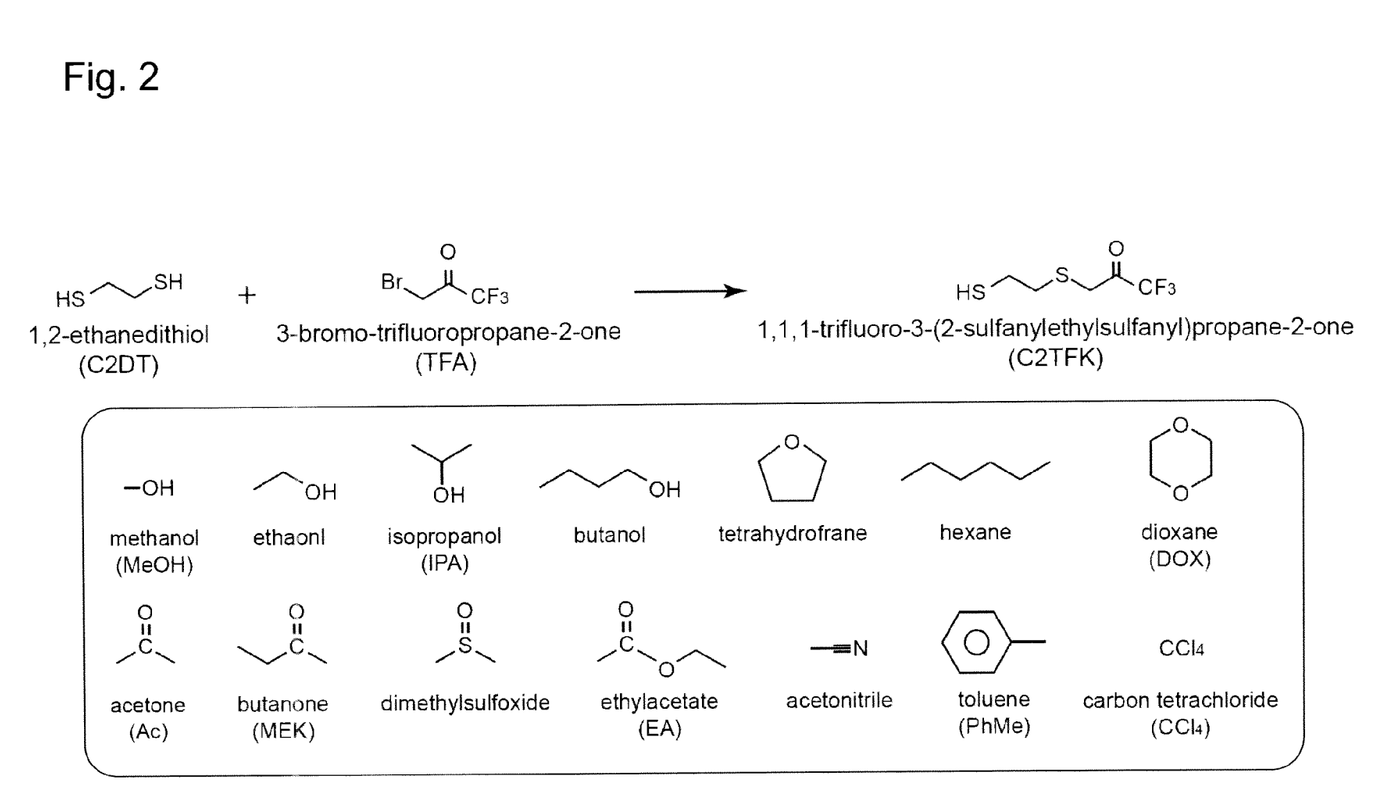
FIG. 2 shows the structures of 14 types of solvent used for synthesis of trifluoroketone (C2TFK) having thiol groups.

FIG. 2 shows the synthetic pathway for 1,1,1-trifluoro-3-(2-sulfanylethylsulfanyl)propane-2-one (C2TFK), which is TFK having thiol groups and 14 types of organic solvent examined as solvents for the synthetic reaction. Each solvent was deoxidized and then 1,2-ethanedithiol (C2DT) and 3-bromo-trifluoropropane-2-one (TFA) were dissolved in the resultant at 1.00 M and 1.05 M, respectively. The solution was stirred under a nitrogen atmosphere at room temperature for 48 hours.

The GMA membrane with a degree of grafting of 130% was immersed at room temperature in the solution after stirring, so that the epoxy groups in the GMA membrane were converted to C2TFK groups. The molar conversion rate from epoxy groups to TFK groups was defined by the following formula (2), and it was then calculated based on an increase in the weight of the membrane (measured before and after immersion). The thus obtained membrane was designated as a C2TFK (x, y) membrane, wherein x and y were solvents used for reaction and for the molar conversion rate, respectively. Subsequently, all epoxy groups that had remained in the membrane were converted to diol groups, thereby resulting in a C2TFK-diol (x, y) membrane.

The membrane to which trifluoroketone had been bound was immersed in 0.50 M sulfuric acid at 60° C. for 3 hours, so that the remaining epoxy groups were converted to diol groups (conversion to diol).

Formula 1

$$\text{Degree of grafting [\%]}=100 \text{ (mass of GMA chain introduced)/(mass of PE membrane)} \quad (1)$$

Formula 2

$$\text{Molar conversion rate [\%]}=100 \text{ (number of moles of TFK groups introduced)/(number of moles of epoxy groups before reaction)} \quad (2)$$

2. Evaluation of the Selective Cauxin Removal Performance (for Selectively Removing Cauxin from Cat Urine) of a Porous Hollow-fiber Membrane with TFK Immobilized thereto Male cat urine was filtered through a filter (pore size: 0.22 µm) to remove the precipitate. Subsequently, artificial urine (2.0 w/w % urea and 0.80 w/w% NaCl) was added to dilute the resultant 3-fold, bovine serum albumin (BSA) was added to 0.20 mg/mL, and thus a supply solution was prepared. The supply solution was caused to penetrate from the internal surface to the external surface of the membrane equilibrated in advance with artificial urine, at a constant flow rate (10 mL/h). Here, the effluent from the external surface of the membrane was collected, a protein contained in the effluent was quantified by a Bradford method, and thus a breakthrough curve was produced. The dynamic adsorption capacity was defined as the value obtained by dividing the amount of cauxin adsorbed (until the breakthrough of cauxin) by the volume of the GMA membrane and calculated by the following formula (3).

Formula 3

$$\text{Dynamic adsorption capacity [mg/mL-GMA fiber]} = \int_0^{V_d}(C_0-C)dv/V \quad (3)$$

Here, $C_0$, $C$, $V_d$, and $V$ are the protein concentration in a supply solution, the protein concentration in an effluent, the amount of the effluent until the breakthrough of cauxin, and the volume of the membrane, respectively.

3. Comparison of Selective Cauxin Removal Performances (for Selectively Removing Cauxin) of Porous Hollow-fiber Membranes with TFK Immobilized thereto and Varying Solvents A precipitate was removed from cat urine by a method similar to that in 2 above so that a supply solution was prepared. The solution was caused to penetrate the C2TFK-diol (IPA, 36) membrane and the C2TFK-diol ($CCl_4$, 36) membrane. Thus, a breakthrough curve with respect to proteins in cat urine was produced. For evaluation, a method similar to that in 2 above was employed.

Results

1. It was Determined that Isopropanol was Used as a Solvent for C2TFK Synthesis

C2DT and TFA were dissolved in all solvents. Upon addition of TFA to solvents, white smoke was generated when TFA was added to dimethylformamide and dimethylsulfoxide. Furthermore, in solutions in which dimethylsulfoxide, acetonitrile, and hexane had been used as solvents, precipitation took place after 48 hours of stirring. If a solution after stirring can be directly used for immobilization of C2TFK, the step of purification of C2TFK can be omitted from the preparation steps. Hence, precipitation after reaction is not preferred.

Figure 3:
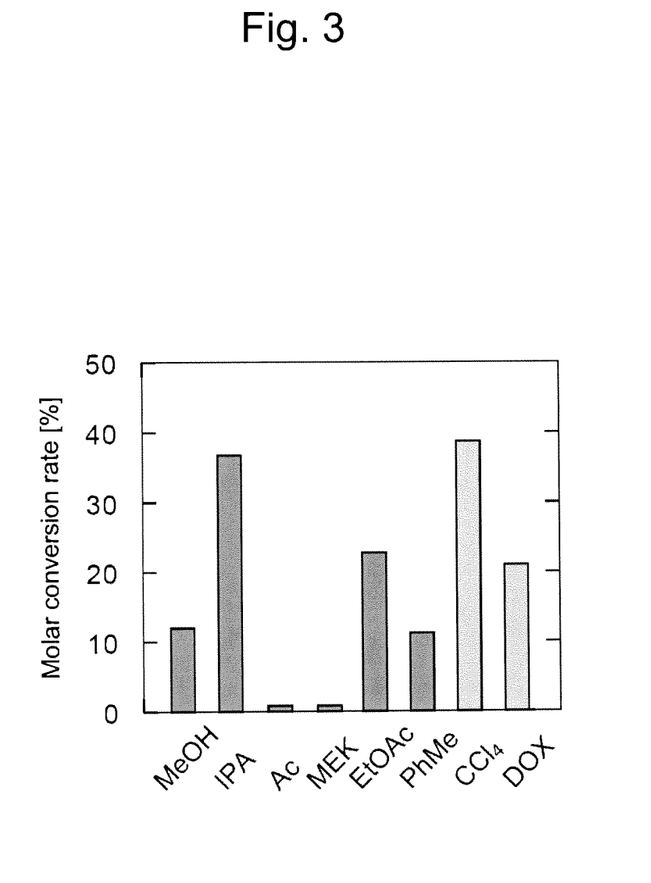
FIG. 3 shows the relationship between solvents used for preparation of C2TFK membranes and the molar conversion rates.

GMA membranes were immersed for 48 hours in C2TFK solutions prepared using 8 types of solvent (methanol (MeOH), isopropanol (IPA), acetone (Ac), methyl ethyl ketone (MEK), ethyl acetate (EtOAc), toluene (PhMe), carbon tetrachloride ($CCl_4$), and dioxane (DOX)) that had not resulted in precipitation after reaction. FIG. 3 shows the resulting molar conversion rates. Except for carbon tetrachloride, which is problematic in terms of environment safety, the solvent found to have the highest molar conversion rate (36%) was IPA. Meanwhile, the molar conversion rates when the other 6 types of solvent had been used were 25% or less.

Figure 4:
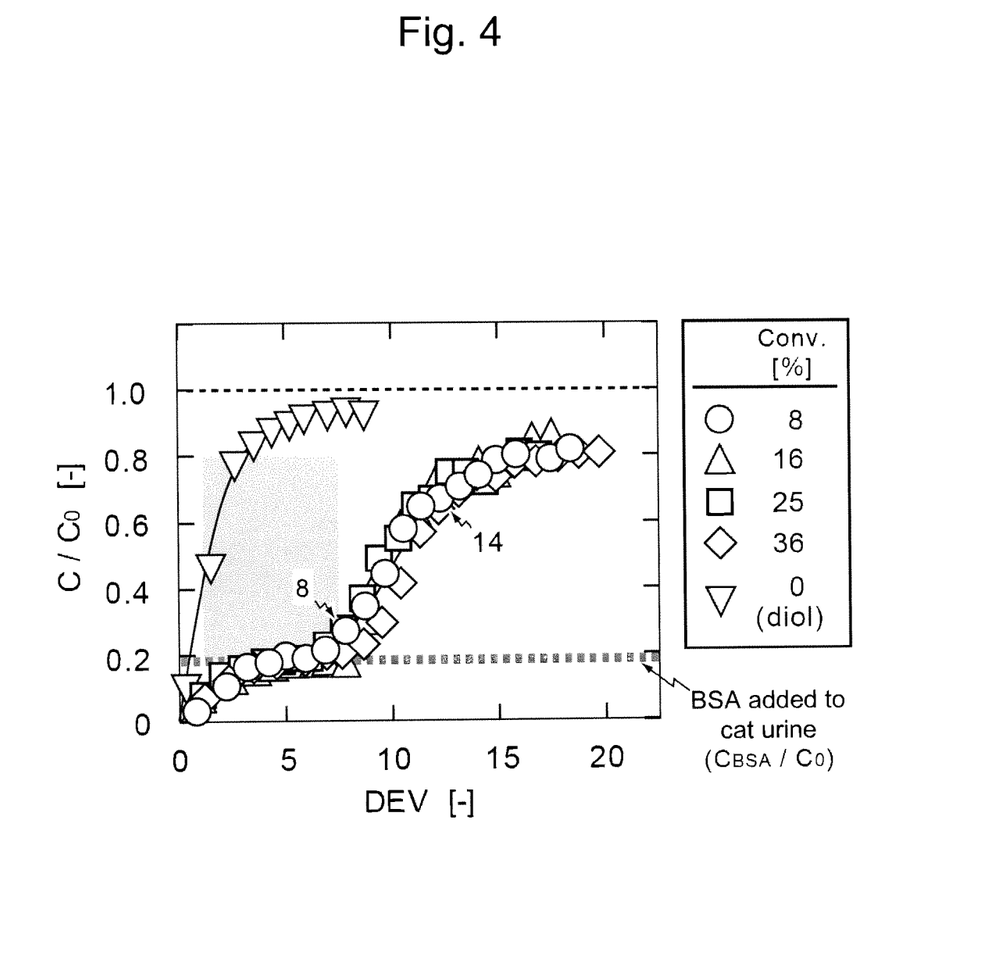
FIG. 4 shows breakthrough curves with respect to proteins in solutions to be supplied to the C2TFK membrane.

2. Cauxin was Able to be Selectively Removed from a Supply Solution by the C2TFK-diol (IPA, y) Membrane C2TFK-diol (IPA, 8-36) membranes (C2TFK group density: 80-360 µmol/cm³) could be prepared by varying the time of immersion of GMA membranes in C2TFK solutions. FIG. 4 shows the breakthrough curves of the C2TFK-diol (IPA, 8-36) membranes with respect to proteins in supply solutions. Along the vertical axis and the horizontal axis of the breakthrough curves, a value obtained by dividing the protein concentration (C) in each effluent by the same ($C_0$) in a supply solution, and a value (DEV) obtained by dividing the volume of a solution that had penetrated by the volume of the membrane, were plotted. Breakthrough curves were almost the same regardless of molar conversion rates. Proteins in each supply solution conducted breakthrough immediately after penetration, $C/C_0$ increased to $C/C_0=0.2$ corresponding to BSA concentration and remained at a constant level for 3 to 7 fractions. Thereafter, $C/C_0$ increased to $C/C_0=0.8$ and then remained at a constant level. On the other hand, in the case of the diol membrane, $C/C_0$ increased to $C/C_0=0.9$ and then remained at a constant level.

Figure 5:
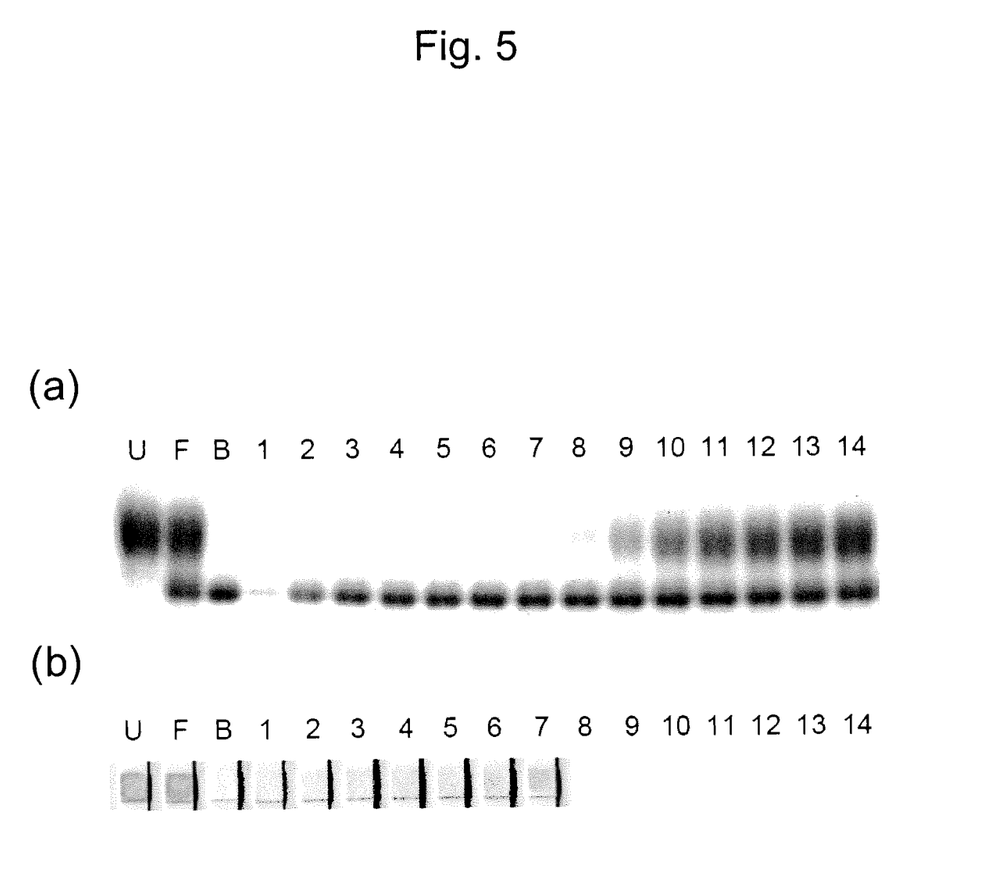

Protein distribution in an effluent from the C2TFK-diol (IPA, 8%) membrane with a molar conversion rate of 8% and the intensity of CE activity are shown in FIG. 5(a) and (b). FIG. 5(a) shows protein distribution in an effluent, as analyzed by SDS-PAGE. FIG. 5(b) shows the intensity of carboxylesterase activity as evaluated using test paper strips. In FIG. 5(b), lane U, lane F, and lane B indicate cat urine, a supply solution, and a BSA solution, respectively. Lanes 1 to 14 indicate the fraction numbers of effluents. The bands of proteins contained in cat urine appeared in the $8^{th}$ and following fractions. Meanwhile, all BSA bands appeared for all fractions. Also, the CE activity of proteins in effluents appeared in the $7^{th}$ and following fractions.

The band of a protein contained in cat urine and CE activity appeared in almost the same fractions. Accordingly, the protein contained in cat urine was cauxin. No cauxin band was observed before the $7^{th}$ fraction. Thus, it was revealed that the C2TFK-diol membrane can specifically remove cauxin. Furthermore, with an effluent from the diol membrane, cauxin bands were observed for all fractions. It was thus revealed that the C2TFK group removes cauxin.

The breakthrough curve did not reach $C/C_0=1$, since a suspension generated in a supply solution was filtered through the membrane. As calculated on the basis of assumption that the breakthrough curve reached $C/C_0=0.8$; that is, equilibrium, the cauxin dynamic adsorption capacity per membrane volume up to the $7^{th}$ fraction was 0.77 mg/mL. With 1.0 mL of the C2TFK-diol membrane, 1.5 mL of cat urine with an average cauxin concentration can be treated. Hence, the cauxin dynamic adsorption capacity is sufficient for treatment of 0.10 mL of cat urine required for evaluation with a test paper strip. The time required from the $1^{st}$ fraction to the $7^{th}$ fraction was 4 minutes. Therefore, a high-speed cauxin removal material that enables cat kidney disease diagnosis using test paper strips could be developed.

Figure 6:
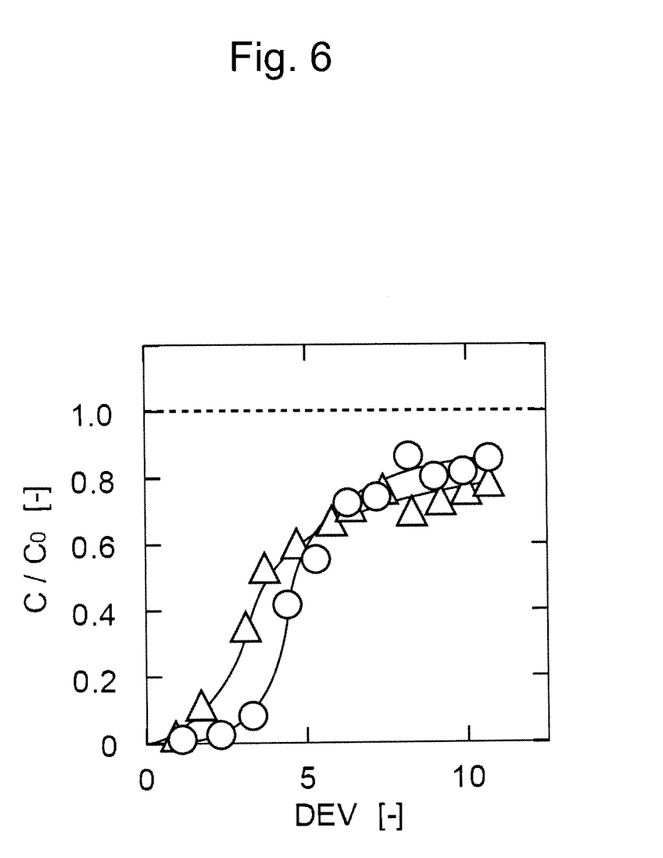
FIG. 6 shows the results of comparing breakthrough curves for the C2TFK membrane when IPA and $CCl_4$ were used as solvents and undiluted cat urine was caused to penetrate the membrane.

3. The Breakthrough Curve of the C2TFK-diol (IPA, 36) Membrane was Identical to that of the C2TFK-diol ($CCl_4$, 38) Membrane FIG. 6 shows breakthrough curves when cat urine was caused to penetrate without dilution. The breakthrough curve of the C2TFK-diol (IPA, 36) membrane was almost identical to that of the C2TFK-diol ($CCl_4$, 38) membrane. It was thus revealed that even when IPA was used as a reaction solvent for C2TFK and C2DT, instead of $CCl_4$, a membrane having cauxin removal performance at almost the same level as that of the other membranes can be prepared.

EXAMPLE 2

Evaluation of the Cauxin Removal Performance (for Removing Cauxin from Cat Urine) of Material for Removing Cauxin Prepared Using as a Substrate a Porous Sheet Methods
1. Reagent and Substrate A porous sheet (INOAC CORPORATION) was used as a substrate membrane. This sheet had a thickness of 2 mm, porosity of 75%, mean pore size of 1-1.5 µm, and specific surface area of 2.6 m$^2$/g. Glycidyl methacrylate (CH$_2$=CCH$_3$COOCH$_2$CHOCH$_2$, hereinafter, abbreviated as GMA) was purchased from NACALAI TESQUE, INC. as a vinyl monomer having epoxy groups and then used as is. 1,2-ethanedithiol (hereinafter, referred to as C2DT) and 3-bromo-1,1,1-trifluoropropane-2-one (hereinafter, referred to as TFA) were each purchased from Wako Pure Chemical Industries, Ltd., Tokyo Chemical Industry Co., Ltd., and Sigma-Aldrich and then used as is. Cat urine and cat serum were collected from domestic male cats, refrigerated or cryopreserved, and then used. Bovine serum albumin (hereinafter, abbreviated as BSA) was purchased from Sigma-Aldrich and then used as is. Regarding urine test paper strips, Pretest Multi II strips were purchased from Wako Pure Chemical Industries, Ltd. and then used.

Figure 7:
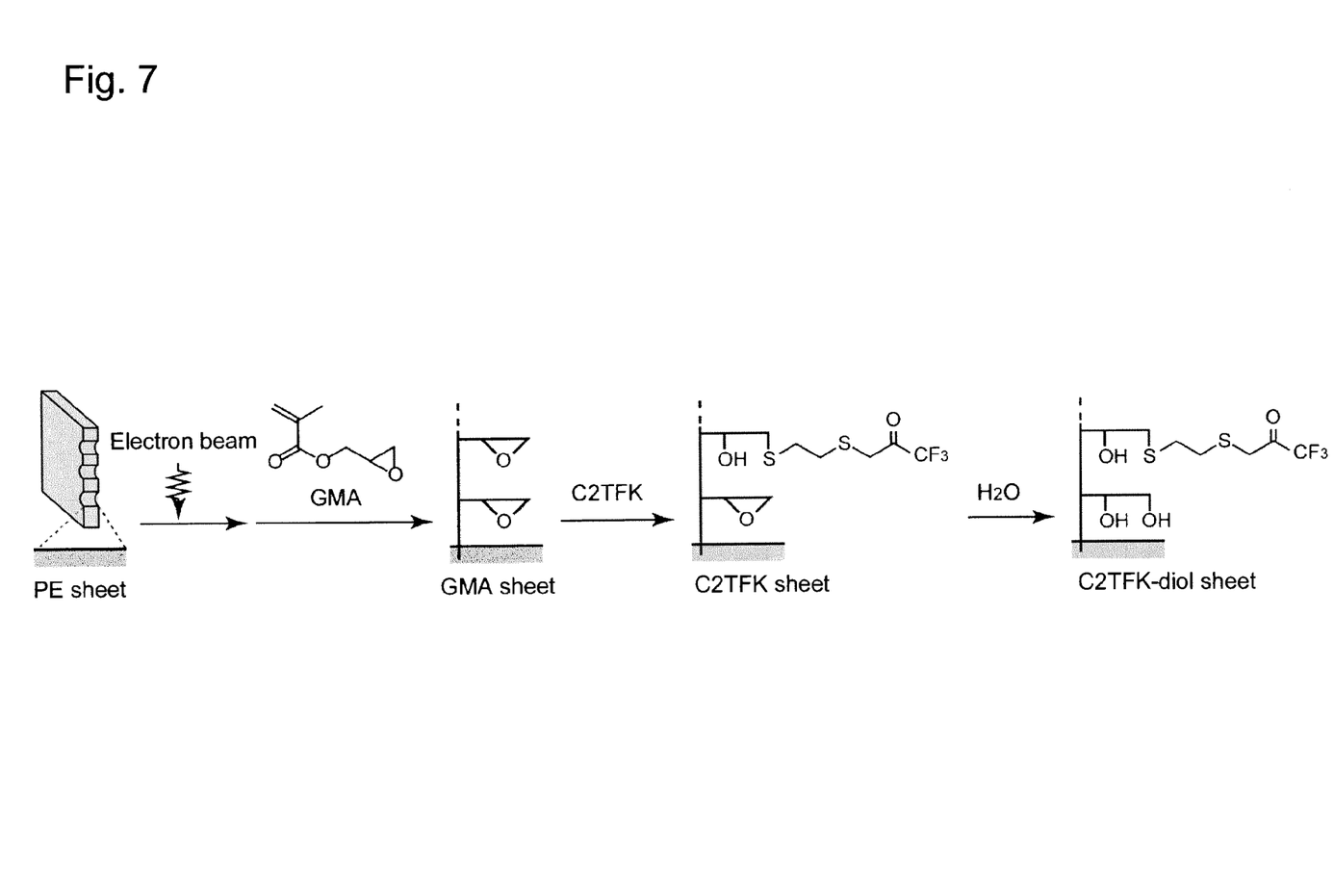
FIG. 7 shows a pathway for immobilization of trifluoroketone to a porous sheet.

2. Preparation of Porous Sheet (C2TFK-diol Sheet) with Trifluoroketone Immobilized thereto FIG. 7 shows the pathway for immobilizing TFK to porous sheets. First, a porous polyethylene sheet was irradiated with an electron beam (200 kGy), so that radicals were generated. Graft polymerization of GMA was performed with the generation of radicals designated as the initiators of the reaction. The thus obtained sheet was designated as a GMA sheet. Here, the degree of grafting (dg) was defined by formula (1) and then calculated from an increase in sheet weight following graft polymerization.

$$\text{Degree of grafting [\%]} = 100(W_1 - W_0)/W_0 \quad (1)$$

Here, $W_0$ and $W_1$ indicate the dry weight [g] of a substrate and the same of a GMA sheet, respectively.

Next, isopropanol was deoxidized by nitrogen bubbling and then C2DT and TFA were dissolved in the solution to 0.10 M and 0.105 M, respectively. The solution was stirred under a nitrogen atmosphere at room temperature for 48 hours. The solution after stirring was designated as a C2TFK solution. The GMA sheet with a degree of grafting of 100% was immersed in the solution for a maximum of 48 hours, so that epoxy groups in the GMA sheet were converted to C2TFK groups. The thus obtained sheet was designated as a C2TFK sheet. The molar conversion rate from epoxy groups to C2TFK groups was defined by formula (2) and then calculated from an increase in sheet weight following graft polymerization.

$$\text{Molar conversion rate [\%]} = 100[(W_2 - W_1)/M]/[(W_1 - W_0)/142] \quad (2)$$

Here, $W_2$ indicates the dry weight [g] of a sheet after introduction of C2TFK groups. Furthermore, 204 and 142 indicate the molecular weight [g/mol] of C2TFK groups and the same of GMA.

For conversion of epoxy groups remaining in the sheet to hydrophilic groups, the C2TFK sheet was immersed in a 0.5 M aqueous H$_2$SO$_4$ solution at 60° C. for 3 hours, so that a sheet in which the remaining epoxy groups had been converted to diol groups was prepared. The thus obtained sheet was referred to as a C2TFK-diol sheet.

3. Evaluation of the Cauxin Removal Performance (for Removing Cauxin from a Model Solution) of a Porous Sheet (C2TFK-diol Sheet) with Trifluoroketone Immobilized thereto To remove a precipitate, male cat urine was centrifuged and then filtered through a filter (pore size: 0.22 µm). Subsequently, artificial urine (2.0 w/w % urea, 0.80 w/w % NaCl, 0.10 w/w % CaCl$_2$, 0.10 w/w % MnCl$_2$) was added to dilute the solution 3-fold. As a serum protein model, bovine serum albumin (BSA) was added to 0.20 mg/mL so as to prepare model urine. Thus, a supply solution was prepared.

The supply solution was caused to penetrate at a constant flow rate of 10 mL/h a sheet that had been equilibrated by permeation with artificial urine. Here, 0.1 mL of a fraction of each effluent was collected. The distribution of a protein contained in each effluent was evaluated by the sodium dodecyl sulfate-polyacrylamide electrophoresis method (hereinafter, abbreviated as an SDS-PAGE method) under non-reducing conditions. For SDS-PAGE, 12 w/w % polyacrylamide gel was used. An effluent (2 µL) was applied to the gel.

Figure 8:
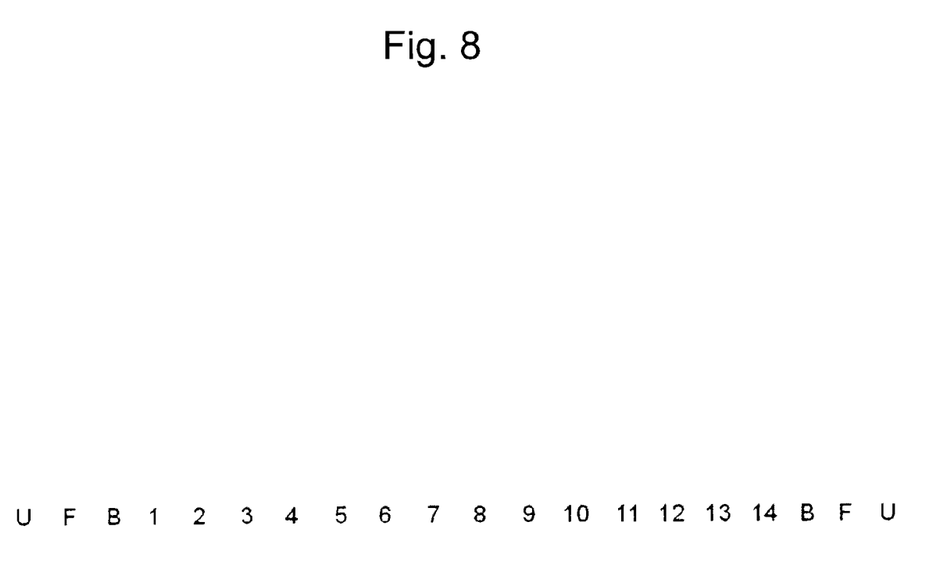
FIG. 8 shows protein distribution in effluents from the C2TFK-diol sheet.

Results and Consideration
1. Evaluation of the Cauxin Removal Performance of Porous Sheet (C2TFK-diol Sheet) with Trifluoroketone Immobilized thereto A supply solution prepared by adding BSA (BSA concentration: 0.2 g/L) to cat urine diluted 3-fold was caused to penetrate the C2TFK-diol sheet with a molar conversion rate of 10% at a constant flow rate (10 mL/h). FIG. 8 shows the results of analyzing protein distribution in effluents by SDS-PAGE. In FIG. 8, lanes indicated by U, F, and B show the results obtained using diluted urine, the above supply solution, and 0.2 g/L BSA solution as samples, respectively. Lanes 1 to 14 show a series of fractions obtained by causing penetration through the C2TFK-diol sheet. Upper bands are cauxin bands and lower bands are BSA bands.

In the case of the C2TFK-diol sheet, cauxin bands become gradually darker from the 1$^{st}$ fraction to the 6$^{th}$ fraction. On the other hand, BSA-derived bands were observed for all fractions of the effluents. These results demonstrate that cauxin was adsorbed to the C2TFH-diol sheet and cauxin was gradually discharged when the amount thereof had exceeded the allowable adsorption amount of cauxin for the C2TFK-diol sheet. Thus, it was revealed that the C2TFK-diol sheet could selectively remove cauxin. Also, the penetration performance (for allowing the penetration of a solution) of the C2TFK-diol sheet was high and thus penetration of the solutions by hand pushing was possible.

Industrial Applicability

The material for removing cat cauxin of the present invention can be used as a material for pretreatment of urine to be used for measurement of urinary proteins for diagnosis of cat kidney disease.

All publications, patents, and patent applications cited herein are incorporated herein by reference in their entirety.

The invention claimed is:

1. A material for removing cauxin in cat urine, wherein 1,1,1-trifluoro-3-(2-sulfanylethylsulfanyl)propane-2-one (C2TFK) having carboxyesterase inhibiting activity is immobilized via dithiol to the surface of a polymer substrate at a density of 50 to 1000 µmol/mL and the material is capable of removing 95% or more of cauxin existing in 50-200 µl of urine from a healthy cat.

2. The material for removing cauxin in cat urine according to claim 1, wherein the polymer substrate is a porous polyethylene hollow-fiber membrane.

3. The material for removing cauxin in cat urine according to claim 1, wherein the polymer substrate is a porous polyethylene sheet.

4. A kit for detecting a urinary protein resulting from cat kidney dysfunction, comprising the material for removing cauxin in cat urine according to claim 1.

5. The material for removing cauxin in cat urine according to claim 1, wherein 1,1,1-trifluoro-3-(2-sulfanylethylsulfanyl)propane-2-one (C2TFK) having carboxyestrase inhibiting activity is immobilized via dithiol to the surface of a polymer substrate at a density of 80-360 µmol/mL and the cauxin dynamic adsorption capacity per membrane volume up to the $7^{th}$ fraction is 0.77 mg/ml.

* * * * *